United States Patent [19]
Rosse et al.

[11] Patent Number: 5,956,125
[45] Date of Patent: Sep. 21, 1999

[54] SYSTEM AND METHOD FOR SCREENING FOR DEMENTIA

[75] Inventors: Richard B. Rosse, Falls Church, Va.; Surendra K. Johri, Gaithersburg; Stephen I. Deutsch, Silver Spring, both of Md.; Barbara L. Schwartz, Washington, D.C.

[73] Assignee: BioProbes, Inc., Gaithersburg, Md.

[21] Appl. No.: 09/100,535

[22] Filed: Jun. 19, 1998

Related U.S. Application Data

[60] Provisional application No. 60/050,222, Jun. 19, 1997.

[51] Int. Cl.⁶ ....................................................... A61B 3/10
[52] U.S. Cl. ........................................... 351/221; 351/246
[58] Field of Search ..................................... 351/246, 247, 351/221, 205, 200

[56] References Cited

U.S. PATENT DOCUMENTS

| | | | |
|---|---|---|---|
| 4,755,043 | 7/1988 | Carter | 351/205 |
| 4,850,691 | 7/1989 | Gardner et al. | 351/221 |
| 5,187,506 | 2/1993 | Carter | 351/221 |
| 5,297,562 | 3/1994 | Potter | 128/898 |
| 5,311,879 | 5/1994 | Yamada et al. | 128/745 |
| 5,345,944 | 9/1994 | Hongo et al. | 128/742 |
| 5,490,098 | 2/1996 | Kardon | 364/580 |
| 5,535,760 | 7/1996 | Potter | 128/898 |
| 5,557,113 | 9/1996 | Moorhouse et al. | 250/559.38 |
| 5,595,883 | 1/1997 | Appleyard et al. | 435/20 |
| 5,617,872 | 4/1997 | Scinto et al. | 128/745 |
| 5,627,612 | 5/1997 | Hayashi | 351/200 |
| 5,646,709 | 7/1997 | Carter | 351/218 |
| 5,661,538 | 8/1997 | Carter | 351/237 |
| 5,692,502 | 12/1997 | Alpert | 128/630 |
| 5,704,369 | 1/1998 | Scinto et al. | 128/745 |

OTHER PUBLICATIONS

Rosse et al., A Measure of Pupillary Oscillation as a Marker of Cocaine–Induced Paranoia, Journal of Neuropsychiatry, vol. 8, No. 3, pp. 347–350 (1996).

Thomas D. Bird, Apolipoprotein E Genotyping in the Diagnosis of Alzheimer's Disease: A Cautionary View, Annals of Neurology, vol. 38, No. 1, pp. 2–3 (1995).

Grünberger et al., Pupillometry in Clinical Psychophysiological Diagnostics: Methodology and Proposals for Application in Psychiatry, Isr J. Psychiatry Relat Sci, vol. 29, No. 2, pp. 100–113 (1992).

Bouma et al., Hippus of the Pupil: Periods of Slow Oscillations of Unknown Origin, Vision Res. vol. 11, pp. 1345–1351 (1971).

Salmon et al., Longitudinal Evaluation of Dementia of the Alzheimer Type: A Comparison of 3 Standardized Mental Status Examinations, Neurology, vol. 40, pp. 1225–1230 (1990).

Currie et al., Eye Movement Abnormalities as a Predictor of the Acquired Immunodeficiency Syndrome Dementia Complex, Arch Neurol, vol. 45, pp. 949–953 (1988).

(List continued on next page.)

*Primary Examiner*—Hung Xuan Dang
*Attorney, Agent, or Firm*—Lerner, David, Littenberg, Krumholz & Mentlik, LLP

[57] ABSTRACT

An easily administered, non-invasive, sensitive and specific system and method for screening persons for dementia, particularly dementia of the Alzheimer's type, is provided. The system and method include means for irradiating the eye of a person with light, preferably light solely within the infrared spectrum, and means for generating a signal responsive to the amount of light reflected from the eye over a period of time. This signal is indicative of changes in the pupil's size over time. The system and method further include means for performing a Fourier transform upon this signal to provide a value indicative of the strength of this signal's frequency components. This value then is compared against a predetermined threshold value and, if this threshold value is exceeded, a higher probability is assigned to the person having dementia, particularly dementia of the Alzheimer's type.

91 Claims, 4 Drawing Sheets

OTHER PUBLICATIONS

Fletcher et al., Saccadic Eye Movement Dysfunction in Alzheimer's Disease, Annals of Neurology, vol. 20, No. 4, pp. 464–470 (1986).

Richard E. Gans, The Eye Clinic Frequently Asked Questions—Alzheimer's Disease, http://ofcn.org/cyber.serv/hwp/hwc/eye/information/faq/alzheimer.html (1994).

American Association for Clinical Chemistry, Eye–Drop Test Unreliable for Diagnosing Alzheimer's, http://aacc.org/cln/profiles/97profiles/01/diagpro9706.html (1996).

Ivanhoe Broadcast News, Inc., Ivanhoe's Medical Breakthroughs—Alzheimer's Eye Test Q&A #962, http://www.ivanhoe.com/docs/backissues/alzheimerseyetestqa.html (1997).

P/S/L Consulting Group Inc., Mayo Jacksonville Study Shows Eye Test Fails as Alzheimer's Diagnosis, http://www.pslgroup.com/dg/2a96a.htm (1997).

Merrill et al., Ocular Motor Abnormalities in Human Immunodeficiency Virus Infection, Annals of Neurology, vol. 30, No. 2, pp. 130–138 (1991).

Applied Science Group, Inc., ASL–About Eye Tracking and Pupillometry, http://world.std.com/~asl/aboutet.html (1997).

SYSTEM AND METHOD FOR SCREENING FOR DEMENTIA

RELATED APPLICATIONS

This application claims the benefit of Provisional Patent Application Serial No. 60/050,222 filed Jun. 19, 1997, the disclosure of which is incorporated herein by reference.

FEDERALLY SPONSORED RESEARCH

The U.S. Government has a paid-up license in this invention and the right in limited circumstances to require the patent owner to license others on reasonable terms as provided under the terms of Grant No. 1 R41 NS36199-01 awarded by the National Institute of Neurological Disorders and Stroke.

FIELD OF THE INVENTION

The present invention pertains to systems and methods for screening a person for dementia and for evaluating his or her probability of having dementia and, more particularly, to systems and methods for screening a person for dementia of the Alzheimer's type and for evaluating his or her probability of having dementia of this type.

BACKGROUND OF THE INVENTION

The number of persons developing dementia or Alzheimer's disease at some point in their lives is enormous and growing with our aging population. As described by Evans et al. (1989), "Alzheimer's disease is a common condition and its public health impact will continue to increase with the increasing longevity of the population." An estimated 10.3% of the population over age 65 has dementia of the Alzheimer's type ("DAT") (Evans et al., 1989). The prevalence of DAT in persons over the age of 85 ranges from about 20% (Selkoe et al., 1992) to over 50% (Evans et al., 1989).

The economic and social impact of DAT also is enormous. The estimated direct cost in the United States for treating DAT in 1991 was $20.6 billion. (Ernst and Hay, 1994.) Assuming that the prevalence of DAT remains constant in the future, a conservative estimate of the economic impact of DAT on the next generation, in discounted present value, is $536 billion for direct costs and $1.75 trillion for both direct and indirect costs. (Ernst and Hay, 1994.)

No easily administered, non-invasive, sensitive and specific test for screening a person for DAT and evaluating his or her probability of having DAT exists today. Such a test could prevent at least some of the disease's adverse economic and social consequences. The potential market for such a test includes neurologists, geriatric psychiatrists, neuropsychologists, gerontologists, primary care physicians, ophthalmologists, optometrists and other health care workers. Clinicians, researchers and pharmaceutical companies also could benefit from an easily administered and inexpensive test for identifying the effectiveness of treatments for DAT. For instance, patients on tacrine (Cognex), donepezil (Aricept) and other cholinergic enhancing medications could be monitored for evaluating the effectiveness of such treatments.

The current tests for evaluating the probability of a person having DAT are expensive and invasive. For instance, single photon computed tomography (SPECT) and positron emission tomography (PET) are costly, require expensive equipment and require the injection of radioactive substances into the body. Such techniques are inappropriate for screening large numbers of persons. Another test includes screening for APOE-Î4 allele which is associated with an increased risk for DAT. Possession of APOE-Î4 allele, however, does not guarantee the presence of DAT, and the absence of APOE-Î4 allele does not rule out DAT. Between 23% and 57% of persons having DAT would be misclassified if possession of APOE-Î4 allele alone were the criterion for diagnosis.

Another test for evaluating the probability of a person having DAT detects the presence of neural thread protein (NTP) from cerebrospinal fluid (CSF). This test claims to be the "first test proven to help physicians be certain in the diagnosis of Alzheimer's disease." This test, however, also is invasive and requires a spinal puncture to obtain a CSF sample.

SUMMARY OF THE INVENTION

The present invention provides an easily administered, non-invasive, sensitive and specific test for screening a person for dementia and evaluating his or her probability of having dementia, particularly dementia of the Alzheimer's type. The inventors have determined that a significant inverse correlation exists between the strength of a person's pupillary oscillations and his or her performance on neuropsychological tests (e.g., mini-mental status examination, dementia rating scale, Boston Naming Test, Weschler Memory Scale (Logical Memory I and II) and "Draw-A-Clock"). The inventors also have determined that the strength of a person's pupillary oscillations accurately discriminates between a person having DAT and a person having normal cognitive function.

In accordance with one aspect of the present invention, a system for screening and evaluating a person for dementia or DAT is provided. The system includes means for measuring the pupil of the eye of the person over a period of time. This means preferably includes means for irradiating the eye with light, preferably light within the infrared spectrum, and means for preventing the eye from receiving light not applied to the eye as a result of this irradiating.

The system further includes means for generating a first signal responsive to light reflected from the eye over a period of time. This means preferably includes a sensor, or a digital or analog camera and a frame grabber, connected to a computer. The computer preferably is a portable computer, and the camera and frame grabber preferably generate a series of pixel images of the eye which are analyzed by the computer over a period of time. The computer preferably counts for each image of the eye the number of pixels within the area of the image representative of the eye's pupil. This count is indicative of the size of the pupil, and changes in this count are indicative of changes in this size.

The system further includes means for generating a second signal indicative of the strength of one or more of the frequency components of the first signal. This second signal may be indicative of the magnitude of these frequency components, the power of these frequency components or some combination of both. This second signal also may be indicative of any other parameter representative of the strength of these frequency components. The means for generating the second signal preferably includes means for performing a Fourier transform, preferably a fast Fourier transform (FFT), upon the first signal for generating these frequency components and preferably also includes means for summing the strengths (e.g., magnitude or power) of these components within a predetermined range of frequencies. This means preferably is a programmed digital computer. The predetermined range of frequencies preferably is between approximately 0 Hz and 40 Hz, more preferably between approximately 0 Hz and 20 Hz and most preferably between approximately 4 Hz and 20 Hz.

The system of the present invention also preferably includes means for identifying the portions of the first signal generated during periods when the person is blinking, and means for ignoring these portions in generating the second signal.

The system also includes means for indicating the probability of the person having dementia, particularly DAT, on the basis of the second signal. This means preferably includes means for assigning a higher probability to the person having dementia, particularly DAT, if the strength of the second signal exceeds a threshold value.

In another aspect, the present invention provides a method for evaluating the probability of a person having dementia, particularly DAT. This method comprises (a) measuring the pupil of an eye of the person over a period of time; (b) generating a first signal responsive to this measuring; (c) generating a second signal indicative of the strength of one or more of the frequency components of the first signal; (d) comparing this strength against a threshold value; and (e) evaluating the probability of the person having dementia or DAT on the basis of this comparison. The method preferably assigns a higher probability to the person having dementia or DAT if the sum of the strengths of the frequency components of the first signal, within a predetermined range of frequencies, exceeds this threshold value.

DESCRIPTION OF THE PREFERRED EMBODIMENTS

Figure 1:
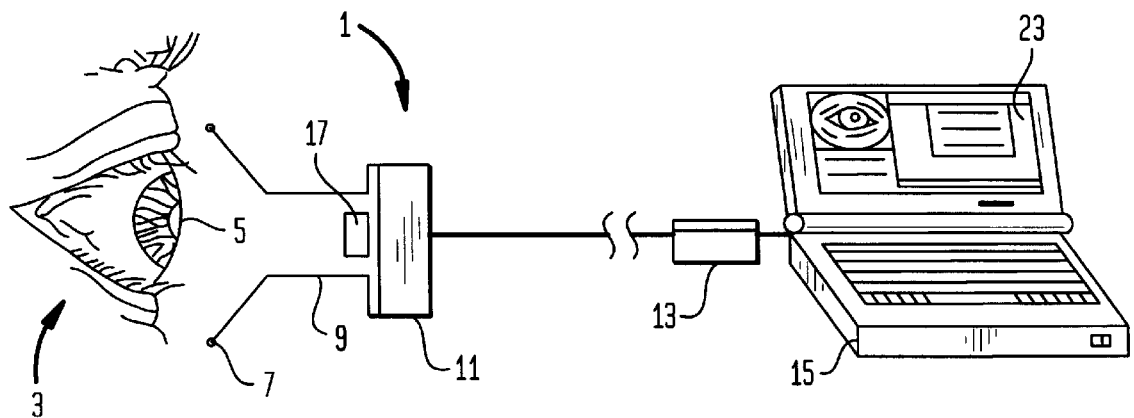
FIG. 1 is a perspective diagram of apparatus in accordance with the present invention.
Figure 2:
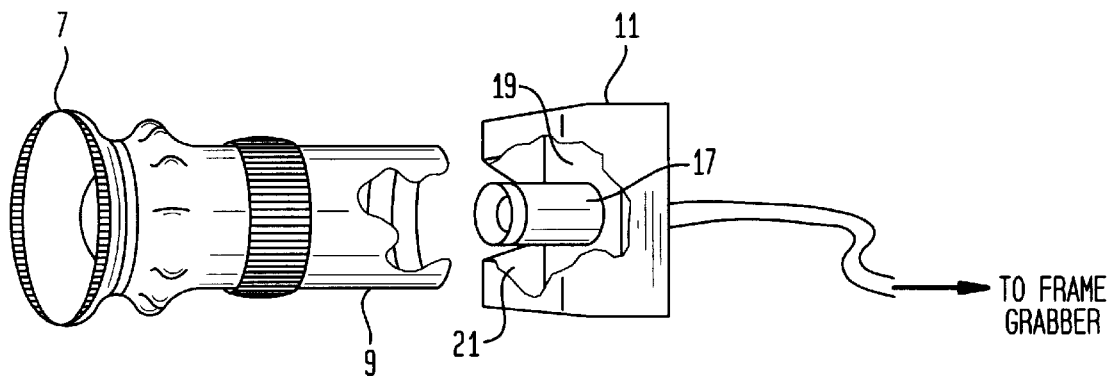
FIG. 2 is a perspective diagram of the optical barrel and camera of the apparatus of FIG. 1.

FIGS. 1 and 2 show the structure of a system 1 in accordance with the present invention. System 1 includes an optical barrel 9 fitted over the lens 17 of a video camera 11. The output of video camera 11 is transmitted to a frame grabber 13 whose output is transmitted to a computer 15 having a display screen 23. Video camera 11 can be any device capable of recording a series of images of the eye and generating a video signal corresponding to these images. In this case, video camera 11 is a black and white, portable CCD (charge coupled device) camera of low lux sensitivity (0.1 lux or less) with an effective pick-up area of 512 pixels (horizontal)×492 pixels (vertical) and a signal-to-noise ratio of 55 dB. In place of video camera 11, a sensor capable of detecting light and generating a signal proportional to the magnitude of the light detected can be used. As used in this specification, the term "light" includes electromagnetic radiation of any wavelength including infrared, visible and ultraviolet wavelengths.

Camera 11 further includes on its face and within the area covered by optical barrel 9 an infrared light source 19. This light source may be, e.g., a light emitting diode or any other device capable of generating and transmitting infrared light into optical barrel 9. This light is transmitted to the eye 3 of a person looking into the optical barrel 9. Eyepiece 7 prevents light other than that transmitted by infrared source 19 from entering optical barrel 9 when the person's eye is pressed against the eyepiece. This eyepiece preferably is made of rubber or some other flexible material capable of conforming to the skin surrounding the eye and preventing light from entering optical barrel 9. In order to facilitate a person's staring into optical barrel 9, a mark may be included either within this barrel, within or on lens 17 or on the face of video camera 11.

In order to reduce ambient light from entering optical barrel 9, a light-absorbing sheet or shield (not shown) can be used to cover the person being tested. Such a sheet or shield could, e.g., be attached to a hat-like garment or shroud to which also is attached optical barrel 9. The room in which the test is conducted also should be as dark as possible, and the lens 17 of video camera 11 should be fitted with a filter 21 for removing light other than that within the frequencies of infrared source 19.

Light transmitted from infrared source 19 is reflected by the person's eye 3 into lens 17 of video camera 11. The amount of light reflected is inversely proportional to the size of the person's pupil 5. If a light sensor is used in place of video camera 11, the magnitude of the signal generated by this sensor is inversely proportional to the size of pupil 5.

Video camera 11 generates a series of pixel images of the eye, including the iris and pupil. Each new image is generated at a sampling rate determined by the camera, e.g., sixty (60) images per second. Video camera 11 transmits these images to a frame grabber 13 which transmits a corresponding series of digital data to computer 15 for analysis. In the alternative, data from video camera 11 can be transmitted directly to computer 15, and a frame grabber can be incorporated within video camera 11 or computer 15. Also, as a further alternative, data from video camera 11, or a light sensor, in analog or digital form, can be transmitted directly to computer 15 for analysis. If in analog form, computer 15 should include an analog to digital (D/A) converter for converting these data to digital form.

Computer 15 preferably is a portable computer for performing testing in the field. On the other hand, computer 15 can be a desk top computer or any general purpose computer capable of analyzing data and running computer programs. In the alternative, computer 15 can be a special purpose device containing only the structure necessary to perform the functions described below (e.g., storage devices, arithmetic unit, comparator, frequency detector, frequency analyzer, etc.). Such a device could be miniaturized and built using, e.g., a microprocessor.

In place of the apparatus shown in FIGS. 1 and 2, a pupil/corneal reflection tracker, such as the RK-426 pupillometer manufactured by ISCAN, Burlington, Mass., can be used to measure the diameter of a person's pupil over a period of time. The data generated by the pupillometer then can be analyzed in accordance with the programs described below using the computing capacity of the pupillometer or a separate computer, such as computer 15. The apparatus described in FIGS. 1 and 2 is considered preferable to the use of a device such as the RK 426, however, because of the size and expense of such a device and the inclusion within it of structure and features unnecessary to the present invention.

Figure 3:
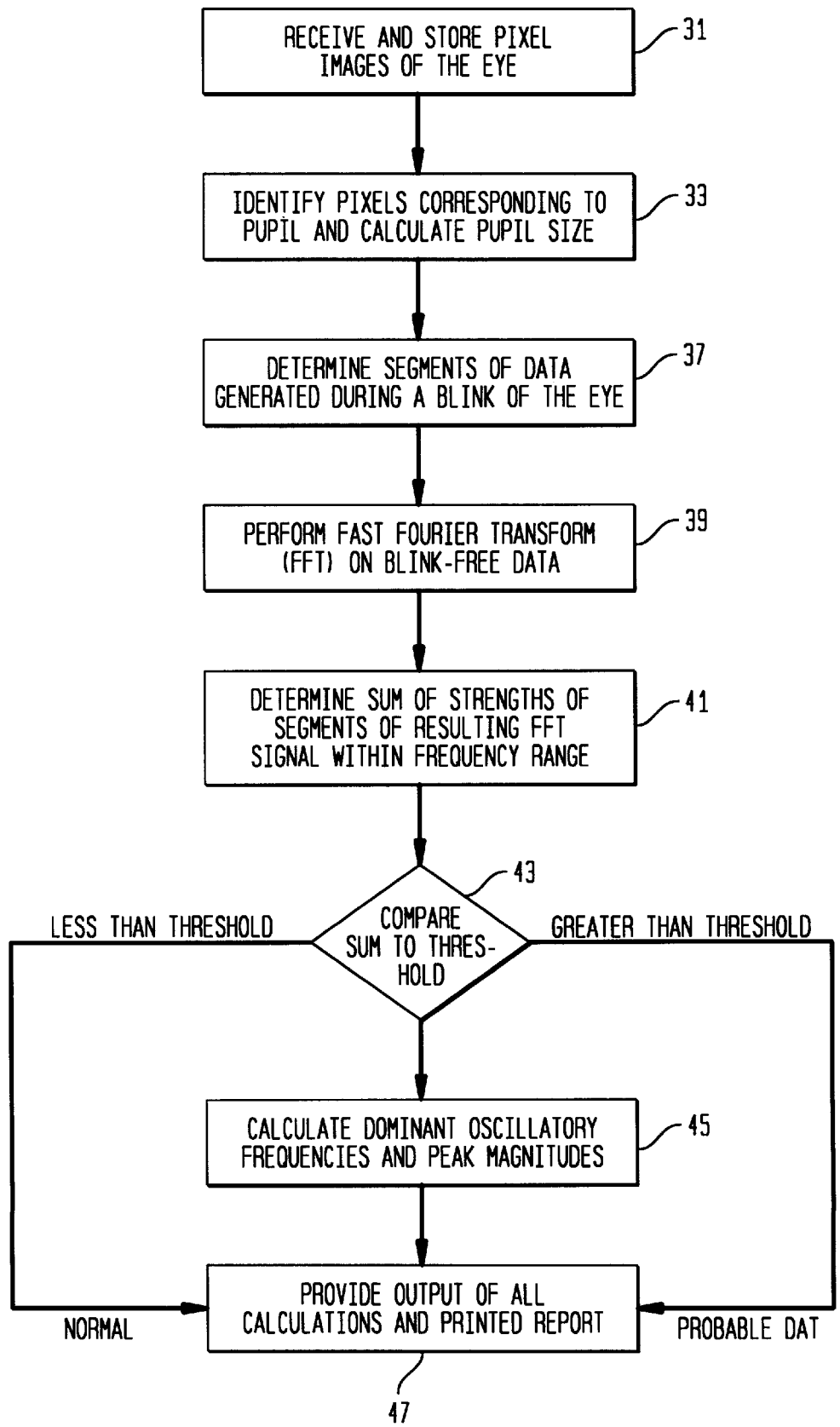
FIG. 3 is a flow diagram of the steps executed by a computer for evaluating the probability of a person having DAT.

A flow diagram of a computer program for analyzing the data transmitted by frame grabber 13 is shown in FIG. 3. At block 31, each pixel image of the eye is received in digital form and temporarily stored. At block 33, the pixels within the area of the image representing the pupil of the eye are identified and used to calculate an instantaneous measure of the pupil's size. Since less light is reflected from the pupil than from other areas of the eye, the intensity of these pixels is substantially less than that of other pixels within each image. By performing a similar calculation for each image, a series of data (a first signal) indicative of the area or diameter of the pupil over a period of time is obtained. This signal also is indicative of the velocity of the pupil's movement.

At block 37, the data generated at block 33 are further analyzed to determine the segments of these data generated during a blink of the eye. These segments are ignored in the further analysis of the data from block 33. The steps executed by the program at block 37 are further discussed in connection with FIG. 4.

At block 39, a fast Fourier transform is performed upon the data (signal) from block 33 (after removal of those portions of the data generated during blinks at block 37). A series of data (a second signal) is generated as a result of this transform. These data provide an indication of the strength of each of the frequency components within the first signal. The fast Fourier transform (FFT) can provide a signal indicative of either the magnitude (in $pixels^2/Hz$) or power (in $pixels^4/Hz$) of these frequency components. The program samples the blink-free data at a prescribed sampling rate, e.g., 60 Hz, for a prescribed period of time (e.g., 30 seconds). For such a sampling rate and sampling period, 1,800 samples of data are provided for the fast Fourier transform. The program acquires these samples of data, performs trend removal (optional) and computes the FFT. A commercially available FFT program for generating a signal indicative of the magnitude of the frequency components is Vu-Point-3 sold by Maxwell Laboratories, Inc., LaJolla, Calif., and a commercially available FFT program for generating a signal indicative of the power of the frequency components is Viewdac, sold by Keithley Instruments, Inc., Tauton, Mass. In addition to performing the FFT, the computer program can, if desired, display on screen 23 (FIG. 1) an instantaneous image of the eye (including blinks) and the first and second signals.

At block 41, the program determines the sum of the strength of all of the contiguous incremental segments of the second signal (generated as a result of the FFT) within a particular frequency range in prescribed increments. This calculation is indicative of the area under the curve of the second signal. These segments can be separated by, e.g., 0.008 Hz, and the prescribed range of frequencies can be between, e.g., 4 Hz and 20 Hz. The range, however, can be any preselected frequency range, including between approximately 0 Hz and 20 Hz or from approximately 0 Hz to 40 Hz. As discussed below, however, the range from between approximately 4 Hz and 20 Hz was found most effective in discriminating between persons with DAT and persons without DAT. The computer code for performing the calculation of block 41 is shown in the Appendix.

At decisional block 43, the sum calculated at block 41 is compared with a threshold value. If this sum is less than the threshold value, the program provides an indication that the person has normal cognitive function. On the other hand, if this sum is greater than this threshold value, the program provides an indication that the person probably has DAT. As discussed below, if the second signal is indicative of the power of the frequency components and the summation of this signal is performed from 4 Hz to 20 Hz in contiguous increments of 0.008 Hz, the threshold value for the total power of pupillary oscillation found to discriminate most effectively between persons with DAT and persons without DAT is 116 $pixels^4/Hz$.

At block 45, the dominant oscillatory frequencies and peak magnitudes are calculated, if desired, and, at block 47, the output of all calculations is provided in a printed report.

Figure 4:
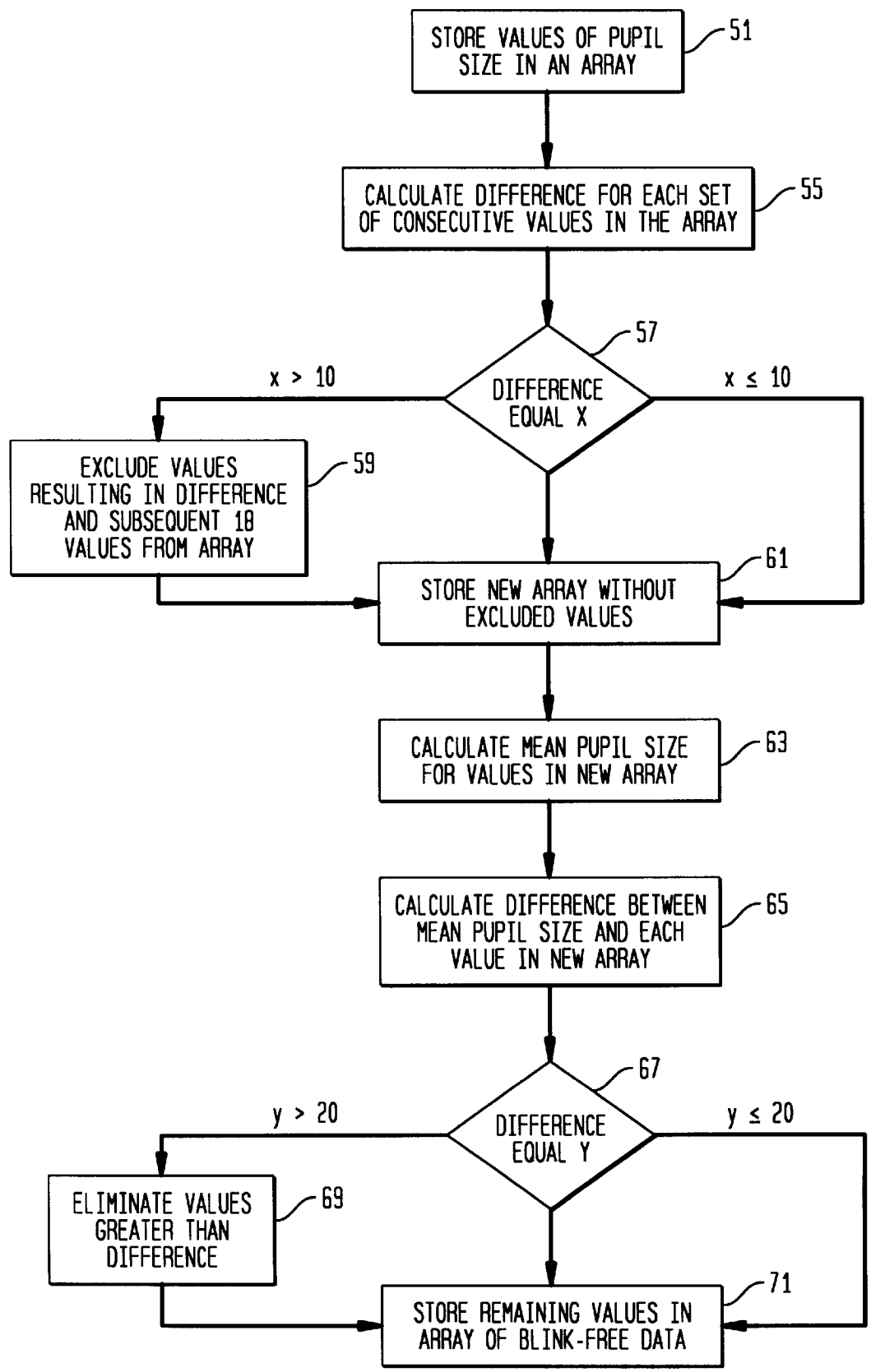
FIG. 4 is a flow diagram of the steps executed by a computer for removing portions of a first signal, indicative of a person's pupil size over time, generated during periods when the person is blinking.

FIG. 4 is a flow diagram of the computer program for removing portions of the first signal generated during blinks of the person's eye. At block 51, each calculated value of the pupil's size is stored in an array. At block 55, the difference between each set of consecutive values in this array is calculated. At block 57, each difference is compared against a predetermined number, e.g., 10, and if all of the differences are less than or equal to 10, the program proceeds directly to block 61 where all of the values in the array are stored in a new array. On the other hand, if one or more of these differences is greater than 10, then, at block 59, for each such difference, the values in the array resulting in such a difference, and the subsequent eighteen values, are excluded from the array. The program then proceeds to block 61 where a new array is stored with all values except the excluded values.

At block 63, the program calculates the mean pupil size (e.g., the mean area or the mean diameter) for all of the samples in the array stored at block 61. At block 65, the program calculates the difference between this mean pupil size and each value in the array. At block 67, each difference is compared against a predetermined value, e.g., 20, and if all of the differences are less than or equal to 20, all of the values in the array stored at block 63 are stored at block 71 as blink-free data. On the other hand, if one or more of these differences is greater than 20, each value corresponding to such a difference is eliminated at block 69, and the remaining values are stored at block 71 as blink-free data.

Using a system in accordance with the present invention, the inventors screened 48 persons over the age of 55 for DAT. Prior to this examination, all persons were administered the following neuropsychological tests: (1) Mini-Mental Status Examination (MMSE) (Folstein et al., 1975); (2) Dementia Rating Scale (DRS) (Mattis, 1988); (3) Boston Naming Test (BNT) (Kaplan et al., 1983); (4) Weschler Memory Scale-Revised (logical memory I and II); (5) category fluency and letter fluency (Benton Multilingual Aphasia Examination); and (6) the Draw-A-Clock Test (Rouleau et al., 1992; Sunderland et al., 1989; Huntzinger et al., 1992). Persons in the study evidencing dementia were given a neuromedical examination, including evaluation of CBC, electrolyte panel, renal panel (BUN and creatinine), thyroid panel (TSH and T4), liver function tests, urinalysis, and serum tests for syphilis, serum $B_{12}$ and folate levels. CT or MRI scans also were evaluated, and a medical history, including a list of medications taken at the time of the examination, were obtained for all persons in the study.

Based upon these neuropsychological and medical evaluations, the persons in the study were assigned to the following groups: (1) suspected DAT; (2) non-DAT dementia; and (3) no evidence of dementia. The suspected DAT group included both persons who probably had DAT and persons who possibly had DAT. Persons in the suspected DAT group had some evidence of dementia, established by either low scores on the MMSE (less than 25) or DRS (less than 125), and/or severe memory deficits exhibited from the results of both the logical memory I and II tests of the Weschler Memory Scale-Revised (scores of 10 or below). Persons having only low scores on the logical memory I and II tests also had either a low score on the category fluency test (less than 10), BNT (less than 45) or the Draw-A-Clock test (less than 6) for assignment to the suspected DAT group.

All persons in the suspected DAT group, therefore, had cognitive deficits in memory function and in at least one other cognitive function. None of the persons assigned to this group had a history of stepwise or sudden worsening of memory or other cognitive functions, or a disturbance of consciousness. Persons assigned to the suspected DAT group, moreover, did not have a systemic (medical) or brain disorder that could account for his or her cognitive impairment. For instance, no clear temporal relationship existed between the onset of the brain disorder and the onset of the person's cognitive problems.

Following these neuropsychological and medical evaluations, each person was placed in a darkened room for three minutes. Using the RK-426 pupillometer, pupil diameters then were determined in the right eye of each person (unless the left eye was preferable for examination because of a cataract, past injury or previous surgery). After pupil diameters in the dark were measured, pupil diameters during light challenge from 5 lux to 700 lux were measured. Dilute tropicamide then was instilled in the eye, and pupil size was measured in the dark and in response to light challenge for the hour following this instillation.

Using the RK-426 pupillometer, pupil diameter for each person then was measured for a period of time under various conditions of ambient light at a sampling rate of 60 Hz. After removing those portions of the data corresponding to blinks, a fast Fourier transform was performed upon the remaining data using Vu-Point-3 software for magnitude analysis and Viewdac software for power analysis. The resulting data corresponding to the strength of the frequency components were summed in segments of 0.008 Hz within the frequency ranges of 0 Hz–4 Hz and 4 Hz–20 Hz to provide an indication of the total strength (power or magnitude) of pupillary oscillations within this frequency range.

This analysis revealed that optimal discrimination among persons occurred when the examination was conducted in the dark and when the total power of pupillary oscillation was calculated for the frequency range of between 4 and 20 Hz. A one-way analysis of variance (ANOVA) for total power of pupillary oscillation in the 4–20 Hz range yielded a significant difference among the three groups (F=7.3; df=2,35; p=0.002; mean of suspected DAT group=230.9; mean of non-DAT dementia group=192.6; mean of non-demented controls=88.5). Pupillary oscillation scores obtained during light challenge also discriminated among the groups (F=3.8; df=2,35; p=0.03), but the use of light challenge did not enhance the ability to discriminate among groups when compared to measurements taken in the dark. The results of this analysis are shown in Table I below.

TABLE I

|  | TPOWH |
| --- | --- |
|  | R-VALUE (P-VALUE) |
| MMSE | −0.47 (0.002) |
| BNT | −0.54 (0.0002) |
| C FLUENCY | −0.35 (0.02) |
| L FLUENCY | −0.32 (0.04) |
| DRS | −0.33 (0.03) |
| WMS-I | −0.32 (0.04) |
| WMS-II | −0.36 (0.01) |
| CLOCK-DRAW | −0.40 (0.008) |

KEY

MMSE = Minimental Status Exam/ BNT = Boston Naming Test
C Fluency = Category Fluency/ L Fluency = Letter Fluency
DRS = Dementia Rating Scale
WMS-I= Weschler Memory Scale- logical stories 1
WMS-II= Weschler Memory Scale- logical stories 2
Clock-Draw = Draw-a-Clock Test
TPOWH = total power of pupillary oscillation in the 4–20 Hz range (pixel$^4$/Hz)

Upon analysis of the data, the inventors determined that a threshold value of 116 pixels$^4$/Hz for total power of pupillary oscillation in the 4–20 Hz range provides optimal discrimination among groups. Using the 116 pixels$^4$/Hz threshold value, the negative predicative power of the test was 100% (i.e., the predicative power to detect people without dementia or non-DAT dementia was 100%). A pupillary oscillation score of less than 116 pixels$^4$/Hz, therefore, predicted the absence of dementia with 100% accuracy. The calculated sensitivity of the test, moreover, was 100%; namely all persons with DAT scored above the threshold value. The specificity of the test was 75%; namely, three quarters of the non-demented persons had pupillary oscillation values below 116 pixels$^4$/Hz. Some of the persons in the false positive group (without suspected DAT but with a total power of pupillary oscillation exceeding 116 pixels$^4$/Hz), however, had some evidence of cognitive impairment. These deficiencies, on the other hand, did not meet the study's criteria for DAT. For instance, one person who tested "false positive" (subject #18) had a low score on logical memory I of the Weschler Memory Scale (in the 12th percentile) but a MMSE of 27 and a DRS of 135. Another person who tested false positive had "normal" cognitive functioning (except for an abnormal Draw-a-Clock test) but had a family history of DAT (subject #12).

The inventors also determined that medications such as beta-blockers do not appear to block the appearance of heightened pupillary oscillations suggestive of DAT. For instance, a person in the study who likely had DAT demonstrated elevated total power of pupillary oscillations notwithstanding that he was taking the beta-blocker propranolol (Inderal). The total power of pupillary oscillation for this person may have been higher, moreover, if he were not taking this beta-blocker.

The results of this study are summarized in Table II below.

TABLE II

| No. | Group | MMSE | BNT | C Fluency | L Fluency | DRS | WMS-I | WMS-II | Clock-Draw | TPOWH |
|---|---|---|---|---|---|---|---|---|---|---|
| 1 | C | 28 | 57 | 20 | 36 | 141 | 68 | 60 | 9 | 263.49 |
| 2 | C | 29 | 58 | 16 | 36 | 135 | 66 | 80 | 9 | 79.0 |
| 3 | A | 20 | 48 | 10 | 36 | 120 | 7 | 8 | 9 | 279.22 |
| 4 | A | 24 | 48 | 9 | 6 | 92 | 2 | 2 | 6 | 119.54 |
| 5 | A | 14 | 30 | 7 | 21 | 96 | 5 | 2 | 2 | 442.07 |
| 6 | C | 24 | 51 | 14 | 30 | 135 | 24 | 46 | 9 | 72.55 |
| 8 | C | 29 | 59 | 16 | 35 | 139 | 60 | 52 | 9 | 97.41 |
| 9 | A | 27 | 40 | 6 | 34 | 132 | 3 | 5 | 8 | 348.1 |
| 10 | C | 27 | −99 | 18 | 29 | 124 | 45 | 40 | 9 | 72.78 |
| 11 | A | 28 | 42 | 12 | 33 | 106 | 12 | 10 | 9 | 139.24 |
| 12 | C | 29 | 58 | 28 | 47 | 137 | 52 | 42 | 6 | 272.32 |
| 13 | B | 21 | 36 | 5 | 13 | 106 | 6 | 2 | 6 | 67.66 |
| 15 | C | 29 | 55 | 20 | 29 | 136 | 82 | 80 | 7 | 186.73 |
| 16 | C | 27 | 48 | 13 | 18 | 133 | 21 | 36 | 8 | 189.79 |
| 17 | C | 28 | 60 | 23 | 38 | 138 | 60 | 78 | 9 | 59.55 |
| 18 | C | 27 | 54 | 21 | 22 | 135 | 12 | 46 | 9 | 129.8 |
| 19 | C | 29 | 52 | 21 | 33 | 140 | 23 | 32 | 6 | 315.95 |
| 20 | C | 29 | 56 | −99 | 44 | 135 | 88 | 87 | 9 | 101.49 |
| 21 | C | 29 | 48 | 17 | 25 | 140 | 96 | 89 | 8 | 55.23 |
| 22 | C | 28 | 54 | 21 | 56 | 138 | 46 | 62 | 10 | 23.11 |
| 23 | C | 29 | 60 | 8 | 36 | 132 | 60 | 60 | 9 | 25.88 |
| 24 | C | 29 | 57 | 18 | 35 | 134 | 65 | 60 | 9 | 56.99 |
| 25 | C | 27 | 58 | 19 | 72 | 138 | 54 | 52 | 9 | 15.08 |
| 26 | C | 27 | 55 | 23 | 19 | 137 | 87 | 65 | 7 | 115 |
| 27 | C | 30 | 58 | 22 | 61 | 140 | 80 | 70 | 10 | 52.33 |
| 28 | C | 24 | 57 | 19 | 21 | 138 | 27 | 40 | 9 | 20.54 |
| 29 | C | 28 | 57 | 15 | 48 | 139 | 12 | 26 | 9 | 17.18 |
| 31 | C | 26 | 55 | 44 | 27 | 137 | 86 | 68 | 9 | 18.46 |
| 32 | C | 28 | 47 | 13 | 23 | 125 | 76 | 53 | 9 | 31.13 |
| 33 | C | 30 | 52 | 52 | 48 | 143 | 92 | 94 | 9 | 26.09 |
| 34 | C | 30 | 58 | 35 | 27 | 128 | 72 | 75 | 9 | 21.74 |
| 35 | C | 30 | 57 | 45 | 54 | 136 | 7 | 26 | 10 | 15.5 |
| 36 | C | 29 | 58 | 40 | 37 | 141 | 68 | 86 | 10 | 54.88 |
| 37 | C | 28 | 57 | 32 | 44 | 138 | 52 | 38 | 8 | 17.47 |
| 38 | WP(A) | 26 | 47 | 22 | 16 | 114 | 12 | 10 | 6 | 171.45 |
| 40 | C | 30 | 55 | −99 | 45 | 135 | 86 | 96 | 9 | 267.46 |
| 41 | A | 23 | 57 | 18 | 38 | 133 | 6 | 8 | 7 | 177.67 |
| 42 | A | 22 | 33 | 6 | 5 | −99 | 6 | 2 | 8 | 170.08 |
| 43 | C | 30 | 56 | 11 | 24 | 132 | 66 | 80 | 8 | 15.32 |
| 44 | C | 29 | 58 | 14 | 26 | 136 | 52 | 56 | 10 | 52.63 |
| 45 | B | 20 | 37 | 10 | 6 | 111 | 6 | 18 | 9 | 472.13 |
| 46 | C | 29 | 55 | 13 | 15 | 135 | 88 | 64 | 9 | 321.82 |
| 47 | B | 25 | 56 | 7 | 38 | 114 | 17 | 8 | 4 | 38.1 |
| 48 | C | 30 | 57 | 11 | 18 | 140 | 74 | 78 | 9 | 73.55 |

KEY
A = Suspected DAT
B = Non-DAT
C = Nondemented controls
WP = Workup in progress
−99 = Missing values
MMSE = Minimental Status Exam/BNT = Boston Naming Test
C Fluency = Category Fluency/L Fluency = Letter Fluency
DRS = Dementia Rating Scale
WMS-I = Weschler Memory Scale- logical stories 1
MWS-II = Weschler Memory Scale- logical stories 2
Clock-Draw = Draw-a-Clock Test
TPOWH = total power of pupillary oscillation in the 4–20 HZ range (pixel$^4$/Hz)

Figure 5:
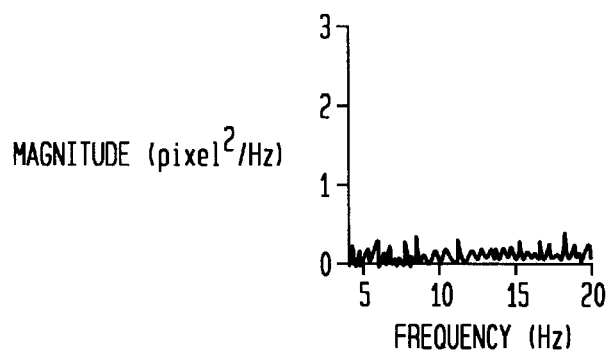
FIG. 5 is a plot of the magnitude of the frequency components of the first signal as a function of frequency for a person with normal cognitive function.
Figure 6:
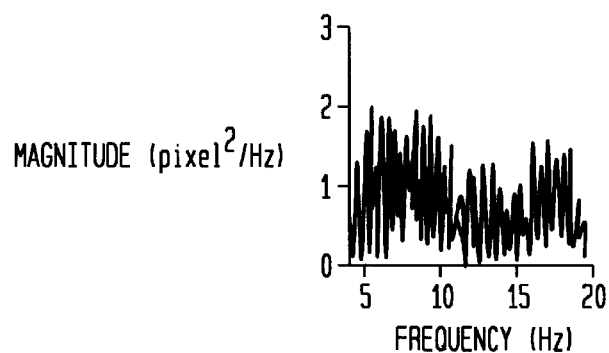
FIG. 6 is a plot of the magnitude of the frequency components of the first signal as a function of frequency for a person having DAT.
Figure 7:
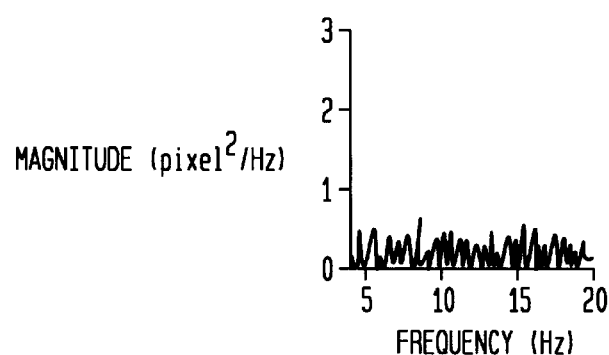
FIG. 7 is a plot of the magnitude of the frequency components of the first signal as a function of frequency for a person having mild dementia as a result of a deficiency in Vitamin $B_{12}$ (not as a result of DAT).
Figure 8:
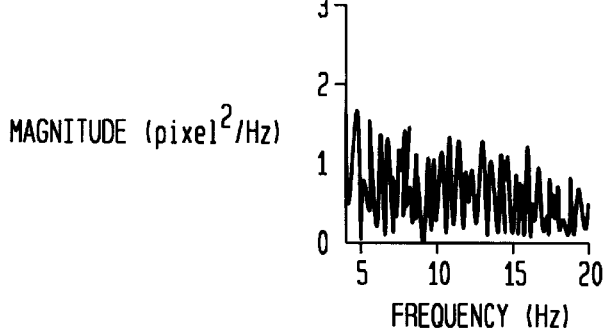
FIG. 8 is a plot of the magnitude of the frequency components of the first signal as a function of frequency for a person having normal cognitive function but a family history of DAT and an inability to pass the Draw-A-Clock test.
Figure 9:
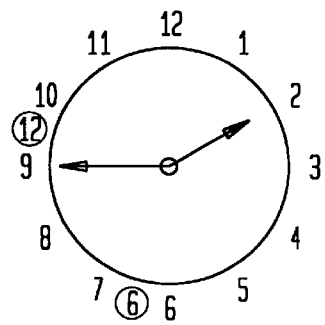
FIG. 9 shows the results of the Draw-A-Clock test for the person referenced in connection with FIG. 8.

The results of this study also are illustrated in FIGS. 5–9. FIG. 5 is a plot of the magnitude of the frequency components (in pixels$^2$/Hz) for the frequency range of 4 Hz–20 Hz for a person in the study with normal cognitive function. FIG. 6 is a similar plot for a person suspected of having DAT; FIG. 7 is a similar plot for a person having mild dementia as a result of a deficiency in Vitamin $B_{12}$ (not as a result of DAT); and FIG. 8 is a similar plot for a person having normal cognitive function but having a family history of DAT and an inability to pass the Draw-A-Clock test. FIG. 9 shows the results of the Draw-A-Clock test for this person (the extra numbers drawn by this person on the clock's face are circled).

This study suggests, therefore, that a determination of the strength of pupillary oscillations is useful in the identification and discrimination of patients with suspected DAT. In such patients, the power and magnitude of pupillary oscillations are increased. A significant correlation also exists between neuropsychological test scores and the strength of pupillary oscillations.

The increase in the strength of pupillary oscillations in persons suspected of DAT may be related to central cholinergic failure. Diminished cholinergic tone to the pupil could result in increased pupillary oscillations produced by unopposed sympathetic stimulation. Cholinergic failure has been observed in the Edinger-Westphal nucleus of DAT patients. This nucleus is important to the regulation of pupil size, and pathology in the nucleus could account for the increase in pupillary oscillations observed in the study. The finding in the study that tropicamide instillation significantly increases the total power of pupillary oscillations in the suspected DAT group by about 150% (from a mean total power of 239.4 pixels$^4$/Hz to a mean total power of 811.9 pixels$^4$/Hz) is consistent with this theory. The tropicamide-induced changes in total power for persons not evidencing dementia were less than in persons suspected of having DAT. The preferred embodiments described above include numerous variations and combinations which are within the spirit and scope of the invention. The foregoing description should be understood as an illustration of the invention, therefore, rather than as a limitation. The scope of the invention is described by the following claims.

APPENDIX

```
C       This program is for extracting the measures of pupillary
C       oscillations after fft has been done on the raw data.
        PARAMETER(J = 1040,IJ = 14)
        DIMENSION PMAGN(J),FREQ(J)
        CHARACTER*12 ABCD(IJ),FILEN
        OPEN(5,FILE = 'BF.R')
        OPEN(6,FILE = 'BF.W')
C       Step-1: Reading and storing the frequency and magnitude
C       numbers in arrays DO 2 N = 1,IJ
        READ(5,13)ABCD(N)
13      FORMAT(27X,A12)
        IF(N.EQ.1)THEN
        FILEN = ABCD(N)
        END IF
2       CONTINUE
        IP = 0
32      CONTINUE
        IP = IP + 1
        READ(5,*,END = 34)FREQ(IP),PMAGN(IP)
        GO TO 32
34      CONTINUE
        IPOINTS = IP
        SUM24F = 0
        B24 = 0.01
C       Step2a: Finding out the peak magnitude in 0–4 HZ range
C       by using 'AMAX1' function.

DO 87 IN = 1,IPOINTS
        PS24F = PMAGN(IN)**2
        IF((FREQ(IN).GT.0.0).AND.(FREQ(IN).LE.4.0))THEN
C       Step 4a: Summation of magnitudes in 0–4 Hz range i.e.
C       calculating area under the curve in 0–4 Hz range SUM24F = SUM24F + PS24F
        B24 = AMAX1(B24,PMAGN(IN))
        ELSE
        GO TO 87
        END IF
87      CONTINUE
C       Step 3a: Finding out the dominant frequency in 0–4 Hz range
        DO 88 I = 1,IPOINTS IF(FREQ(I).GT.0.0).AND.(FREQ(I).LE.4.0))THEN
        CONTINUE
        ELSE
        GO TO 88
        END IF
        IF (PMAGN(I).EQ.B24)THEN
        A24 = FREQ(I)
        ELSE
        GO TO 88
        END IF
88      CONTINUE
C       Step:2b Finding out the peak magnitude in 4–20 Hz range
C       by using 'AMAX1' function SUM420F = 0
        B420 = 0.01
        DO 89 IN = 1,IPOINTS
        PS420F = PMAGN(IN)**2
        IF((FREQ(IN).GT.4.0).AND.(FREQ(IN).LE.20.0))THEN
```

APPENDIX -continued

```
C       Step 4b: Summation of magnitudes in 4–20 Hz range i.e.
C       calculating area under the curve in 4–20 Hz range SUM420F = SUM420F + PS420F
        B420= AMAX1(B420,PMAGN(IN))
        ELSE
        GO TO 89
        END IF
89      CONTINUE
C       Step 3b: Finding out the dominant frequency in 0–4 Hz range DO 90 I = 1,IPOINTS
        IF((FREQ(I).GT.4.0).AND.(FREQ(I).LE.20.0))THEN
        CONTINUE
        ELSE
        GO TO 90
        END IF
        IF(PMAGN(I).EQ.B420)THEN
        A420 = FREQ(I)
        ELSE
        GO TO 90
        END IF
90      CONTINUE
C       Step 5: Writing the outcome measures in a file for further processing
C       WRITE(6,17)FILEN,B0,A0,SUM0F
C       WRITE(6,17)FILEN,B2,A2,SUM2F
C       WRITE(6,17)FILEN,B4,A4,SUM4F
C       WRITE(6,17)FILEN,B6,A6,SUM6F
C       WRITE(6,17)FILEN,B8,A8,SUM8F
C       WRITE(6,17)FILEN,B12,A12,SUM12F
        WRITE(6,17)FILEN,B24,A24,SUM24F
        WRITE(6,17)FILEN,B420,A420,SUM420F
C       WRITE(6,15)FILEN,BH,AH,PH,PRODH,PSMH,CENTPH
C       WRITE(6,16)FILEN,RATIO,PRATIO,CRATIO
C    14 FORMAT(A12,1X,F7.2,1X,F6.3,1X,F10.2,1X,F10.2,1X,F10.2,1X,
        F5.2,
C       1X,1F10.2)
C    15 FORMAT(A12,1X,F7.2,1X,F6.3,1X,F10.2,1X,F10.2,1X,F10.2,1X,
        F5.2)
C    16 FORMAT(A12,2X,F10.2,2X,F10.2,2X,F10.2)
     17 FORMAT(A12,1X,3F10.2)
C       WRITE(6,14)FILEN,PSM
C    14 FORMAT(A10,2X,2F10.2)
        WRITE(6,21)FILEN,SUM420F
     21 FORMAT(A12,2X,F10.2)
        STOP
        END
```

What is claimed is:

1. A method for indicating the probability of a person having dementia comprising:

(a) irradiating an eye of said person with light;

(b) generating a first signal responsive to light reflected over a period of time from said eye;

(c) generating a second signal indicative of the strength of one or more of the frequency components of said first signal;

(d) comparing said strength against a threshold value; and (e) indicating the probability of said person having dementia on the basis of said comparison.

2. A method as in claim 1, wherein said step of irradiating comprises irradiating said eye with light only within the infrared spectrum.

3. A method as in claim 2, further comprising preventing said eye from receiving light not applied to said eye as a result of said irradiating.

4. A method as in claim 1, wherein said step of generating said first signal comprises generating a series of pixel images of said eye over said period of time and counting the number of pixels within each of said images within the area of said image representative of said pupil.

5. A method as in claim 4, wherein said step of generating said series of pixel images comprises generating said images with a digital CCD camera and a frame grabber.

6. A method as in claim 4, wherein said step of generating said series of pixel images comprises generating said images with an analog camera and a frame grabber.

7. A method as in claim 1, wherein said step of generating said second signal comprises generating said second signal to be indicative of the magnitude of said one or more frequency components.

8. A method as in claim 1, wherein said step of generating said second signal comprises generating said second signal to be indicative of the power of said one or more frequency components.

9. A method as in claim 1, wherein said step of generating said second signal comprises performing a Fourier transform upon said first signal.

10. A method as in claim 9, wherein said step of performing said Fourier transform comprises performing said transform digitally using a computer.

11. A method as in claim 1, wherein said step of generating said second signal comprises summing the strengths of each of said one or more frequency components within a predetermined range of frequencies, and said step of comparing comprises comparing said sum against said threshold value.

12. A method as in claim 11, wherein said predetermined range is between approximately 0 Hz and 40 Hz.

13. A method as in claim 11, wherein said predetermined range is between approximately 0 Hz and 20 Hz.

14. A method as in claim 11, wherein said predetermined range is between approximately 4 Hz and 20 Hz.

15. A method as in claim 11, wherein said step of summing comprises summing the magnitude of each of said one or more frequency components.

16. A method as in claim 11, wherein said step of summing comprises summing the power of each of said one or more frequency components.

17. A method as in claim 1, wherein said step of indicating comprises assigning a higher probability to said person having dementia if said strength exceeds said threshold value.

18. A method as in claim 1, wherein said step of indicating comprises assigning a higher probability to said person having dementia of the Alzheimer's type if said strength exceeds said threshold value.

19. A method as in claim 1, wherein said step of generating said first signal comprises identifying the portions of said first signal generated during a blink of said eye, and said step of generating said second signal comprises removing said portions of said first signal before generating said second signal.

20. A method for indicating the probability of a person having dementia comprising:

(a) measuring the pupil of an eye of said person over a period of time;

(b) generating a first signal responsive to said measuring;

(c) generating a second signal indicative of the strength of one or more of the frequency components of said first signal;

(d) comparing said strength against a threshold value; and (e) indicating the probability of said person having dementia on the basis of said comparison.

21. A method as in claim 20, wherein said step of generating said second signal comprises generating said second signal to be indicative of the magnitude of said one or more frequency components.

22. A method as in claim 20, wherein said step of generating said second signal comprises generating said second signal to be indicative of the power of said one or more frequency components.

23. A method as in claim 20, wherein said step of generating said second signal comprises performing a Fourier transform upon said first signal.

24. A method as in claim 23, wherein said step of performing said Fourier transform comprises performing said transform digitally using a computer.

25. A method as in claim 20, wherein said step of generating said second signal comprises summing the strengths of each of said one or more frequency components within a predetermined range of frequencies, and said step of comparing comprises comparing said sum against said threshold value.

26. A method as in claim 25, wherein said predetermined range is between approximately 0 Hz and 40 Hz.

27. A method as in claim 25, wherein said predetermined range is between approximately 0 Hz and 20 Hz.

28. A method as in claim 25, wherein said predetermined range is between approximately 4 Hz and 20 Hz.

29. A method as in claim 25, wherein said step of summing comprises summing the magnitude of each of said one or more frequency components.

30. A method as in claim 25, wherein said step of summing comprises summing the power of each of said one or more frequency components.

31. A method as in claim 20, wherein said step of indicating comprises assigning a higher probability to said person having dementia if said strength exceeds said threshold value.

32. A method as in claim 20, wherein said step of indicating comprises assigning a higher probability to said person having dementia of the Alzheimer's type if said strength exceeds said threshold value.

33. A system for indicating the probability of a person having dementia comprising:

(a) means for irradiating an eye of said person with light;

(b) means for generating a first signal responsive to light reflected over a period of time from said eye;

(c) means for generating a second signal indicative of the strength of one or more of the frequency components of said first signal; and (d) means for providing an output indicating the probability of said person having dementia on the basis of said strength.

34. A system as in claim 33, wherein said means for irradiating comprises means for irradiating said eye with light only within the infrared spectrum.

35. A system as in claim 34, further comprising means for preventing said eye from receiving light not applied to said eye as a result of said irradiating.

36. A system as in claim 33, wherein said means for generating said first signal comprises means for generating a series of pixel images of said eye over said period of time and means for counting the number of pixels within each of said images within the area of said image representative of said pupil.

37. A system as in claim 36, wherein said means for generating said series of pixel images comprises a digital CCD camera and a frame grabber.

38. A system as in claim 36, wherein said means for generating said series of pixel images comprises an analog camera and a frame grabber.

39. A system as in claim 33, wherein said means for generating said second signal comprises means for generating said second signal to be indicative of the magnitude of said one or more frequency components.

40. A system as in claim 33, wherein said means for generating said second signal comprises means for generating said second signal to be indicative of the power of said one or more frequency components.

41. A system as in claim 33, wherein said means for generating said second signal comprises means for performing a Fourier transform upon said first signal.

42. A system as in claim 41, wherein said means of performing said Fourier transform comprises a programmed digital computer.

43. A system as in claim 33, wherein said means for generating said second signal comprises means for summing the strengths of each of said one or more frequency components within a predetermined range of frequencies, and said means for providing said output comprises means for comparing said sum against a threshold value.

44. A system as in claim 43, wherein said predetermined range is between approximately 0 Hz and 40 Hz.

45. A system as in claim 43, wherein said predetermined range is between approximately 0 Hz and 20 Hz.

46. A system as in claim 43, wherein said predetermined range is between approximately 4 Hz and 20 Hz.

47. A system as in claim 43, wherein said means for summing comprises means for summing the magnitude of each of said one or more frequency components.

48. A system as in claim 43, wherein said means for summing comprises means for summing the power of each of said one or more frequency components.

49. A system as in claim 33, wherein said means for providing said output comprises means for assigning a higher probability to said person having dementia if said strength exceeds a threshold value.

50. A system as in claim 33, wherein said means for providing said output comprises means for assigning a higher probability to said person having dementia of the Alzheimer's type if said strength exceeds a threshold value.

51. A system as in claim 33, wherein said means for generating said first signal comprises means for identifying the portions of said first signal generated during a blink of said eye, and said means for generating said second signal comprises means for removing said portions of said first signal before generating said second signal.

52. A system for indicating the probability of a person having dementia comprising:
   (a) means for determining the size of the pupil of an eye of said person over a period of time;
   (b) means for generating a first signal indicative of said size over said period;
   (c) means for generating a second signal indicative of the strength of one or more of the frequency components of said first signal;
   (d) means for providing an output indicating the probability of said person having dementia on the basis of said strength.

53. A system as in claim 52, wherein said means for generating said second signal comprises means for generating said second signal to be indicative of the magnitude of said one or more frequency components.

54. A system as in claim 52, wherein said means for generating said second signal comprises means for generating said second signal to be indicative of the power of said one or more frequency components.

55. A system as in claim 52, wherein said means for generating said second signal comprises means for performing a Fourier transform upon said first signal.

56. A system as in claim 55, wherein said means for performing said Fourier transform comprises a programmed digital computer.

57. A system as in claim 52, wherein said means for generating said second signal comprises means for summing the strengths of each of said one or more frequency components within a predetermined range of frequencies, and said means for providing said output comprises means for providing said output on the basis of said sum.

58. A system as in claim 57, wherein said predetermined range is between approximately 0 Hz and 40 Hz.

59. A system as in claim 57, wherein said predetermined range is between approximately 0 Hz and 20 Hz.

60. A system as in claim 57, wherein said predetermined range is between approximately 4 Hz and 20 Hz.

61. A system as in claim 57, wherein said means for summing comprises means for summing the magnitude of each of said one or more frequency components.

62. A system as in claim 57, wherein said means for summing comprises means for summing the powers of each of said one or more frequency components.

63. A system as in claim 52, wherein said means for providing said output comprises means for assigning a higher probability to said person having dementia if said strength exceeds a threshold value.

64. A system as in claim 52, wherein said means for providing said output comprises means for assigning a higher probability to said person having dementia of the Alzheimer's type if said strength exceeds a threshold value.

65. An apparatus for indicating the probability of a person having dementia, said apparatus comprising:
   (a) a light source positioned to irradiate an eye of said person;
   (b) a light detector positioned to detect light reflected from said eye, said light detector producing an output representative of the amount of light reflected from said eye;
   (c) a frequency analyzer having an input and providing an output, said input of said frequency analyzer coupled to said output of said light detector, said output of said frequency analyzer providing the strength of one or more of the frequency components of said output of said light detector;
   (d) a comparator having first and second inputs and providing an output, said first input of said comparator coupled to said output of said frequency detector, said second input of said comparator coupled to a predetermined value and said output of said comparator providing an indication of the probability of said person having dementia.

66. An apparatus as in claim 65, wherein said light source emits light only within the infrared spectrum.

67. An apparatus as in claim 66, further comprising a shield positioned to prevent said eye from receiving light not emitted from said light source.

68. An apparatus as in claim 65, wherein said light detector includes a camera positioned to generate a series of pixel images of said eye.

69. An apparatus as in claim 68, further including a counter coupled to said camera to provide a count of the number of pixels within each of said images within the area of said image representative of the pupil of said eye, and wherein said output of said light detector is representative of said number.

70. An apparatus as in claim 65, wherein said frequency analyzer performs a Fourier transform upon said output of said light detector to produce said one or more frequency components.

71. An apparatus as in claim 70, wherein said output of said frequency analyzer is indicative of the magnitude of said one or more frequency components.

72. An apparatus as in claim 70, wherein said output of said frequency analyzer is indicative of the power of said one or more frequency components.

73. An apparatus as in claim 70, wherein said frequency analyzer includes a summer to sum the strengths of said one or more frequency components within a predetermined range of frequencies, and said output of said frequency analyzer provides said sum.

74. An apparatus as in claim 73, wherein said predetermined range is between approximately 0 Hz and 40 Hz.

75. An apparatus as in claim 73, wherein said predetermined range is between approximately 0 Hz and 20 Hz.

76. An apparatus as in claim 73, wherein said predetermined range is between approximately 4 Hz and 20 Hz.

77. An apparatus as in claim 65, wherein said output of said comparator provides an indication of a higher probability of said person having dementia if said output of said frequency analyzer exceeds said predetermined value.

78. An apparatus as in claim 65, wherein said output of said comparator provides an indication of a higher probability of said person having dementia of the Alzheimer's type if said output of said frequency analyzer exceeds said predetermined value.

79. An apparatus for indicating the probability of a person having dementia, comprising:
   (a) a pupillometer positioned to determine the size of the pupil of an eye of said person over a period of time and to provide an output indicative of said size over said period; and
   (b) a computer, coupled to said output of said pupillometer, programmed to determine the strength of one or more of the frequency components of said output and to provide an output indicative of the probability of said person having dementia on the basis of said strength.

80. An apparatus as in claim 79, wherein said computer is programmed to determine the magnitude of said one or more frequency components.

81. An apparatus as in claim 79, wherein said computer is programmed to determine the power of said one or more frequency components.

82. An apparatus as in claim 79, wherein said computer is programmed to perform a Fourier transform upon said output of said pupillometer.

83. An apparatus as in claim 79, wherein said computer is programmed to sum the strength of each of said one or more frequency components within a predetermined range of frequencies and to provide said output indicative of the probability of said person having dementia on the basis of said sum.

84. An apparatus as in claim 83, wherein said predetermined range is between approximately 0 Hz and 40 Hz.

85. An apparatus as in claim 83, wherein said predetermined range is between approximately 0 Hz and 20 Hz.

86. An apparatus as in claim 83, wherein said predetermined range is between approximately 4 Hz and 20 Hz.

87. An apparatus as in claim 83, wherein said computer is programmed to sum the magnitude of each of said one or more frequency components.

88. An apparatus as in claim 83, wherein said computer is programmed to sum the powers of each of said one or more frequency components.

89. An apparatus as in claim 79, wherein said computer is programmed to compare said strength against a threshold value and to provide said output indicative of the probability of said person having dementia on the basis of said comparison.

90. An apparatus as in claim 79, wherein said computer is programmed to provide an output indicating a higher probability of said person having dementia if said strength exceeds a threshold value.

91. An apparatus as in claim 79, wherein said computer is programmed to provide a signal indicating a higher probability of said person having dementia of the Alzheimer's type if said strength exceeds a threshold value.

\* \* \* \* \*

UNITED STATES PATENT AND TRADEMARK OFFICE
CERTIFICATE OF CORRECTION

| | | |
|---|---|---|
| PATENT NO. | : | 5,956,125 |
| DATED | : | September 21, 1999 |
| INVENTOR(S) | : | Rosse et al. |

It is certified that error appears in the above-identified patent and that said Letters Patent is hereby corrected as shown below:

Column 10, Table II, second line of entries, column 11, "79.0" should read "79.05"

Signed and Sealed this

Sixteenth Day of May, 2000

Attest:

Q. TODD DICKINSON

*Attesting Officer*                *Director of Patents and Trademarks*